United States Patent [19]
Jubin, Jr. et al.

[11] Patent Number: 5,840,933
[45] Date of Patent: Nov. 24, 1998

[54] CATALYTIC CONVERTER SYSTEM AND PROGRESS

[75] Inventors: John C. Jubin, Jr., West Chester; W. Wayne Wentzheimer, Glen Mills, both of Pa.

[73] Assignee: Arco Chemical Technology, L.P., Greenville, Del.

[21] Appl. No.: 740,461

[22] Filed: Oct. 29, 1996

[51] Int. Cl.$^6$ .................................................. C07D 301/19
[52] U.S. Cl. ............................................................ 549/529
[58] Field of Search ............................................. 549/529

[56] References Cited

U.S. PATENT DOCUMENTS

| | | | |
|---|---|---|---|
| 3,351,635 | 11/1967 | Kollar | 260/348.5 L |
| 3,829,392 | 8/1974 | Wulff | 252/430 |
| 3,923,843 | 12/1975 | Wulff | 260/348.5 L |
| 4,021,454 | 5/1977 | Wulff et al. | 260/348.5 L |
| 4,367,342 | 1/1983 | Wulff et al. | 549/529 |

FOREIGN PATENT DOCUMENTS

| | | |
|---|---|---|
| 0323663 | 7/1989 | European Pat. Off. . |
| 1249079 | 10/1971 | United Kingdom . |

*Primary Examiner*—Ba K. Trinh
*Attorney, Agent, or Firm*—Stephen D. Harper; William C. Long

[57] ABSTRACT

A reactor and process is for the production of oxirane compounds by reaction of an olefin such as propylene with an organic hydroperoxide using a solid contact catalyst, characterized by the following features:

(1) the reactor is divided into a series of separate zones, each zone containing a bed of solid epoxidation catalyst;

(2) conditions are maintained so as to provide the liquid phase without substantial vapor formation throughout the entire reactor;

(3) cold reactor feed is provided which is preheated to reaction temperature by separate indirect heat exchange with reaction liquid from various of the separate reactor zones;

(4) reaction liquid from the last of the series of reaction zones is reduced in pressure to form a gas-liquid mixture at a lower temperature, and this gas liquid mixture is heated by indirect heat exchange with the reaction liquid from at least one of the separate reactor zones.

3 Claims, 1 Drawing Sheet

5,840,933

CATALYTIC CONVERTER SYSTEM AND PROGRESS

FIELD OF THE INVENTION

The present invention relates to a catalytic converter system and a process for carrying out highly exothermic reactions between liquid reactants, such as the reaction between propylene and ethylbenzene hydroperoxide to form propylene oxide, using a solid heterogeneous catalyst.

DESCRIPTION OF THE PRIOR ART

Substantial difficulties are encountered in carrying out highly exothermic reactions where reactants and/or products are temperature sensitive. For example, the catalytic liquid phase reaction of propylene and an organic hydroperoxide to produce propylene oxide is a highly exothermic reaction and the reaction selectivity to the desired product is quite temperature sensitive. Thus, removal of the exothermic heat of reaction without causing excess temperature rise presents a serious problem.

Conventional reactors for exothermic reactions are usually of two types:

(1) Quench type which consist of multiple fixed beds with cold feed quench injected in between beds (2) Tubular type in which the catalyst is placed in the tubes of a vertical shell and tube heat exchanger If the heat of reaction is high, the first type does not provide sufficient heat removal. This can be overcome by recycling cold reactor effluent but this results in the disadvantages associated with back-mixed reactors.

The tubular reactor cost becomes prohibitive when high heat of reaction have to be removed through heat exchanger surfaces operating with a low heat transfer coefficient. There is also a temperature gradient from the center of the tube which is often detrimental to a process which requires nearly isothermal conditions.

European Patent 0 323 663 describes a fixed bed catalytic reactor and process for carrying out the epoxidation of an olefin by reaction with an organic hydroperoxide at substantially isothermal conditions. As described in this European Patent, all heat generated by the exothermic reaction is removed by vaporization of the low boiling reaction mixture component, propylene in the case of a propylene/organic hydroperoxide system. Sufficient propylene is fed to the reactor to remove all of the reaction exotherm. The reactor is operated at the boiling pressure of the reaction mixture in such a manner as to provide a cocurrent downflow of a liquid and a gas phase. The procedure is said to represent an improvement over the then currently employed methods involving a multi-reactor discipline with interstage cooling.

The procedure and apparatus described in European Patent 0 323 663 has a number of severe disadvantages. Where the reaction exotherm is removed by vaporization of propylene as required in the European Patent, excessive amounts of propylene must be fed as liquid to the system. In fact, the European Patent shows feeding 16.67 moles of propylene per mole of ethyl benzene hydroperoxide to the reactor. When it is considered that the epoxidation is essentially equimolar as to propylene and hydroperoxide, it can be appreciated that the procedure of the European Patent necessarily involves recovery and recycle of high volumes of propylene at great expense.

Additionally, although European Patent 0 323 663 appears to describe reactor outlet pressure of 26 bar (about 377 psia), this would not appear consistent with the vapor pressure of the liquid reaction mixture. More likely, the actual outlet pressure would be 150 psia or less and this results in the additional and very important problem of refrigeration and/or recompression of the large propylene recycle stream.

A further problem with the system of European Patent 0 323 663 is the poor reaction selectivity which would result at the low propylene concentrations in the liquid phase in the lower part of the reactor.

BRIEF DESCRIPTION OF THE INVENTION

In accordance with the invention, a reactor and process is provided which is especially useful for the production of oxirane compounds by reaction of an olefin such as propylene with an organic hydroperoxide using a solid contact catalyst, the invention being characterized by the following features:

(1) the reactor is divided into a series of separate zones, each zone containing a bed of solid epoxidation catalyst;

(2) conditions are maintained so as to provide the liquid phase without substantial vapor formation throughout the entire reactor;

(3) cold reactor feed is provided which is preheated to reaction temperature by separate indirect heat exchange with reaction liquid from various of the separate reactor zones;

(4) reaction liquid from the last of the series of reaction zones is reduced in pressure to form a gas-liquid mixture at a lower temperature, and this gas liquid mixture is heated by indirect heat exchange with the reaction liquid from at least one of the separate reactor zones.

DESCRIPTION OF THE DRAWINGS

The attached Figure which is a schemematic representation of the process and apparatus claimed herein illustrates the invention.

DETAILED DESCRIPTION

Figure 1:
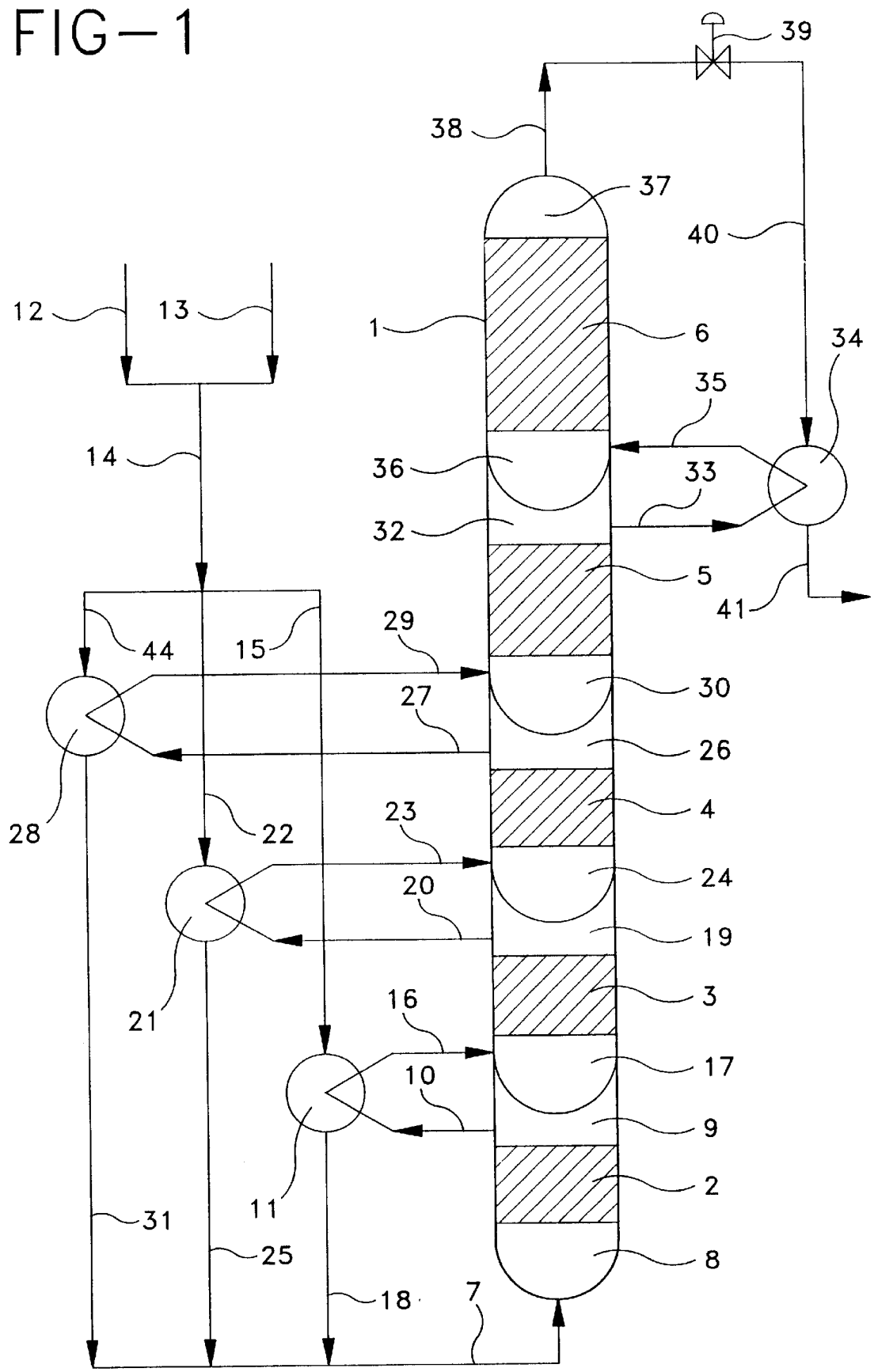

Practice of the invention is especially applicable to highly exothermic reactions such as that between an olefin, eg. propylene, and an organic hydroperoxide, eg. ethylbenzene hydroperoxide, and can best be described with reference to the accompanying drawing.

Referring to the drawing, reactor 1 is a vertical cylindrical reactor having five separate beds of solid heterogenous epoxidation catalyst, catalyst beds 2, 3, 4, 5 and 6. Retaining means are provided (not shown) to support the solid catalyst in place while permitting passage of liquid therethrough.

A liquid reaction mixture comprised of propylene and ethylbenzene hydroperoxide which has been preheated to reaction temperature is introduced via line 7 to lower zone 8 of the reactor. As shown in the drawing, upflow of the reaction mixture takes place but liquid downflow is equally feasible.

The reaction mixture passes from zone 8 through catalyst bed 2 herein propylene oxide is formed by reaction of propylene and ethylbenzene hydroperoxide in accordance with known procedures. Conditions are regulated to provide a modest temperature rise, eg. 10°–50° F., as a result of the reaction exotherm in bed 2.

The reaction mixture from catalyst bed 2 passes to zone 9 from which zone it is withdrawn from reactor 1 via line 10 and passed to indirect heat exchanger 11.

Relatively cold, eg. 80°–120° F., feed propylene and ethylbenzene oxidate which contains ethylbenzene hydroperoxide are fed via lines 12 and 13 respectively, and then as a combined stream via line 14 to the system. A portion of this cold feed passes to exchanger 11 via line 15 wherein it is heated by indirect heat exchange to reaction temperature. The cooled reaction mixture from which the exothermic heat of reaction has been removed passes via line 16 to zone 17 of reactor 1 while the preheated feed passes to zone 8 of reactor 1 via lines 18 and 7.

From zone 17, the reaction liquid passes through catalyst bed 3 wherein further reaction of propylene and ethylbenzene hydroperoxide takes place to form propylene oxide. Again, conditions are controlled to provide a modest temperature rise, eg. 10°–50° F., as a result of the reaction exotherm in bed 3.

The reaction mixture from catalyst bed 3 passes to zone 19 from which zone it is withdrawn from reactor 1 via line 20 and passed to indirect heat exchanger 21.

A second portion of the relatively cold feed passes via line 22 to exchanger 21 wherein it is heated by indirect heat exchange to reaction temperature. The cooled reaction mixture from which the exothermic heat of reaction has been removed passes via line 23 to zone 24 of reactor 1 while the preheated feed passes to zone 8 of reactor 1 via lines 25 and 7.

From zone 24, the reaction liquid passes through catalyst bed 4 wherein further reaction of propylene and ethylbenzene hydroperoxide takes place to form propylene oxide. Conditions are controlled to provide a modest temperature rise, eg. 10°–50° F., as a result of the reaction exotherm in bed 4.

The reaction mixture from catalyst bed 4 passes to zone 26 from which zone it is withdrawn from reactor 1 via line 27 and passed to indirect heat exchanger 28.

The remainder of the relatively cold feed passes via line 44 to exchanger 28 wherein it is heated by indirect heat exchange to reaction temperature. The cooled reaction mixture from which the exothermic heat of reaction has been removed passes via line 29 to zone 30 of reactor 1 while the preheated feed passes to zone 8 of reactor 1 via lines 31 and 7.

From zone 30, the liquid reaction mixture passes through catalyst bed 5 wherein further reaction of propylene and ethylbenzene hydroperoxide takes place to form propylene oxide. There is a modest temperature use, eg. 10°–50° F., as a result of the reaction exotherm in bed 5.

The reaction mixture from catalyst bed 5 passes to zone 32 from which zone it is withdrawn from reactor 1 via line 33 and passed to indirect heat exchanger 34.

In exchanger 34, the reaction mixture from bed 5 is cooled and the exothermic heat of reaction removed by indirect heat exchange and the cooled reaction mixture passes via line 35 to zone 36 of reactor 1.

From zone 36, the reaction mixture passes through catalyst bed 6 wherein final reaction of propylene and ethylbenzene hydroperoxide takes place to form propylene oxide. Throughout reactor 1 the pressure is maintained at an elevated level to avoid substantial vaporization of the components of the reaction mixture. Illustrative pressures maintained throughout reactor 1 are generally in the range 500 to 800 psia. In catalyst bed 6 there is a modest temperature rise, eg. 10°–50° F., as a result of the reaction exotherm in bed 6.

The reaction mixture passes through catalyst bed 6 to zone 37 and is removed from reactor 1 via line 38. The removed mixture, which is essentially liquid, passes through pressure reducing means where the pressure is reduced to a value at which there is vaporization of the lighter component, eg. propylene, and temperature reduction by reason of the vaporization to a level which is substantially lower, eg. 30°–60° F. below the temperature of the reaction mixture removed from zone 32 via line 33. As illustrated in the drawing, a control valve 39 can be used to accomplish the pressure reduction resulting in a mixed phase in line 40. Generally, pressure is reduced from that maintained in reactor 1 to about 250 to 350 psia in order to achieve the vaporization and temperature reduction.

The vapor and liquid reaction product mixture passes via line 40 to exchanger 34 wherein by indirect heat exchange the mixture is heated with the exothermic heat of reaction from bed 5. The reaction mixture from zone 32 from which the exotherm has been removed passes via line 35 to zone 36 of reactor 1 as described above.

As a result of the indirect heat exchange in exchanger 34, heat necessary to separate $C_3$ components such as propylene from the heavier components of the mixture in subsequent conventional distillation operation is transferred from the reaction mixture from zone 32 to the vapor/liquid mixture in line 40. Without the described pressure reduction via means 39 and accompanying temperature reduction, the appropriate heat transfer could not take place.

The heated vapor and liquid product mixture passes from exchanger 34 via line 41 for separation of the various components in accordance with known procedures.

The epoxidation reaction of the present invention is carried out in accordance with known conditions. See, for example, U.S. Pat. No. 3,351,635, the disclosure of which is incorporated herein by reference.

Generally reaction temperatures are in the range of 150° F. to 250 F., usually 180° F. to 225° F., and pressures are sufficient to maintain the liquid phase in reactor 1, eg. 500 to 800 psia.

In general, the temperature increase in the several reaction zones is maintained at a modest level, eg. 10° to 50° F. in order to achieve high reaction selectivity. Generally it is advantageous to cool the reaction mixture from each zone to about the temperature of the feed to the reactor in order to approach isothermal reaction conditions.

Known solid heterogeneous catalysts are employed. In this regard, reference is made to European patent publication 0 323 663, to UK 1,249,079, to U.S. Pat. No. 4,367,342, 3,829,392, 3,923,843 and 4,021,454 the disclosures of which are incorporated herein.

The invention is especially applicable to epoxidation of alpha olefins having 3–5 carbon atoms with aralkyl hydroperoxide.

The following example illustrates an especially preferred practice of the invention as described in the accompanying drawing.

Referring to the drawing, propylene feed at about 100° F. and 700 psia is introduced via line 13 at the rate of about 794,072 lbs/hr. Ethylbenzene oxidate also at 100° F. and 700 psia is introduced via line 12 at the rate of about 560,000 lbs/hr. The feed streams are combined in line 14.

The feed stream is divided with a portion passed to heat. exchangers 11, 21 and 28. About 473,926 lbs/hr passes via line 15; to heat exchanger 11 wherein it is heated to about 195° F. by indirect heat exchange with the reaction mixture from zone 9 of reactor 1.

About 473,926 lbs/hr of the feed passes via line 22 to heal exchanger 21 wherein it is heated to about 195° F. by indirect heat exchange with the reaction mixture from zone 19 of reactor 1.

The remaining portion of the feed 406,221 lbs/hr, passes via line 44 to heat exchanger 28 wherein it is heated to about 195° F. by indirect heat exchange with the reaction mixture from zone 26 of reactor 1.

The preheated feed streams are recombined and fed via line 7 to zone 8 of reactor 1 at 195° F. and 570 psia.

Reactor 1 is a vertical cylindrical reactor having five separate zones containing separate beds 2, 3, 4, 5 and 6 of solid heterogeneous epoxidation catalyst which was prepared as described in Example VII of Netherlands Patent 145,233.

The feed liquid is introduced into zone 8 and passes through catalyst bed 2 whereby the exothermic reaction of ethylbenzene hydroperoxide and propylene takes place to form propylene oxide. The reaction liquid passes through bed 2 to zone 9 and then at 224.8° F. and 700 psia the liquid passes via line 10 to heat exchanger 11 wherein by indirect heat exchange a portion of the feed to the reactor is heated as above described.

The reaction mixture from which the reaction exotherm from bed 2 has been removed passes at about 197.6° F. and 700 psia via line 16 to zone 17 of reactor 1. From zone 17, the reaction mixture passes through catalyst bed 3 wherein further exothermic reaction of ethylbenzene hydroperoxide and propylene takes place to form propylene oxide. From catalyst bed 3, the reaction mixture passes to zone 19 and then at 225.3° F. and 675 psia the mixture passes via line 20 to heat exchanger 21. In exchanger 21, a portion of the reactor feed is heated to reaction conditions as above described by indirect heat exchange with the reaction mixture.

The reaction mixture from which the reaction exotherm from bed 3 has been removed passes at about 198.2° F. and 675 psia via line 23 to zone 24 of reactor 1. From zone 24, the reaction mixture passes through catalyst bed 4 whereby the further reaction of ethylbenzene hydroperoxide and propylene takes place to form propylene oxide. From catalyst bed 4, the reaction mixture passes to zone 26 and then via line 27 at about 222.8° F. and 650 psia to heat exchanger 28. In exchanger 28, a portion of the reactor feed is heated to reaction conditions as above described by indirect heat exchange with the reaction mixture.

The reaction mixture from which the reaction exotherm from bed 4 has been removed passes at about 199.6° F. and 650 psia via line 29 to zone 30 of reactor 1. From zone 30, the reaction mixture passes through catalyst bed 5 whereby the further reaction of ethylbenzene hydroperoxide and propylene takes place to form propylene oxide. From catalyst bed 5, the reaction mixture passes to zone 32 and thence via line 33 at about 221.6° F. and 650 psia to heat exchanger 34.

In heat exchanger 34, the reaction mixture from zone 32 is cooled by indirect heat exchange with the final reaction mixture from zone 37 which, as will be described, has been reduced in pressure and partially vaporized.

The reaction mixture from which the reaction exotherm from bed 5 has been removed passes at about 198.6° F. and 650 psia via line 35 to zone 36 of reactor 1. From zone 36, the liquid mixture passes through catalyst bed 6 whereby further production of propylene oxide by reaction of propylene with ethylbenzene hydroperoxide takes place. From catalyst bed 6, the liquid reaction mixture passes to zone 37 and is removed from reactor 1 via line 38 at about 223.9° F. and 650 psia.

The liquid reaction mixture passes via line 38 to pressure reduction valve 39 wherein the pressure is reduced from 650 psi to 320 psia. There is partial vaporization of the reaction mixture and as a result of the pressure reduction and partial vaporization, the liquid and vapor temperature decreases to about 170° F.

From reduction valve 39, the vapor and liquid mixture passes via line 40 at about 170° F. and 320 psia to exchanger 34. About 354,669 lbs/hr of vapor and about 999,402 lbs/hr of liquid comprise this mixture.

In exchanger 34, the vapor and liquid from via line 40 are heated by indirect heat exchange with the reaction mixture from zone 32; this heat exchange accomplishes the dual function of removing the exotherm of the reaction in catalyst bed 5 from the feed to zone 36 while at the same time providing to the reaction mixture exiting via line 41 heat necessary to separate in one or more distillation steps lighter components such as the $C_3$ hydrocarbons from the heavier reaction mixture components.

The heated product mixture passes at about 180.6° F. and 320 psia via line 41 to conventional component separation.

The following table gives the weight percentage compositions for the various process streams. The Stream No. designation refers to the process stream in the corresponding line or zone in the attached figure.

TABLE 1

| | Stream Composition wt % | | | | | | |
|---|---|---|---|---|---|---|---|
| Stream No. | 13 | 12 | 14 | 10 | 27 | 33 | 41 |
| Propylene | 90.1 | — | 52.9 | 51.9 | 50.1 | 49.4 | 48.5 |
| Propane | 9.8 | — | 5.8 | 5.8 | 5.8 | 5.8 | 5.8 |
| Ethylbenzene | — | 58.7 | 24.3 | 24.3 | 24.3 | 24.3 | 24.3 |
| Ethylbenzene Hydroperoxide | — | 35.0 | 14.5 | 11.3 | 5.5 | 3.1 | 0.3 |
| Methyl Benzyl Alcohol | — | 6.3 | 2.6 | 5.4 | 10.6 | 12.7 | 15.2 |
| Propylene Oxide | — | — | — | 1.3 | 3.8 | 4.8 | 5.95 |
| By-Product | — | — | — | — | — | — | 0.05 |

In this example, conversion based on hydroperoxide is 98%, and the molar selectivity of propylene to propylene oxide is 99%, thus demonstrating the efficiency and effectiveness of the invention. Costs associated with construction and operation of the system are substantially minimized.

We claim:

1. A process for the catalytic liquid phase exothermic reaction of a $C_3$–$C_5$ olefin with an aralkyl hydroperoxide with comprises passing a mixture containing the olefin and hydroperoxide at reaction conditions of elevated temperature and pressure through a series of separate reaction zones each packed with a bed of solid epoxidation catalyst, removing the liquid reaction mixture from the last of said separate reaction zones, reducing the pressure to provide partial vaporization temperature reduction of the reaction mixture removed from the last of the separate reaction zones, heating the partially vaporized mixture by indirect heat exchange with the reaction mixture from the first or an intermediate reaction zone and heating the feed mixture containing olefin and hydroperoxide by indirect heat exchange with the reaction mixture from the first or an intermediate reaction zone.

2. The process of claim 1 wherein propylene and ethylbenzene hydroperoxide are reacted to form propylene oxide.

3. The process of claim 1 wherein the partially vaporized mixture is heated by indirect heat exchange with the reaction mixture from the next to last reaction zone.

* * * * *